US009513255B2

(12) United States Patent
Beriet et al.

(10) Patent No.: US 9,513,255 B2
(45) Date of Patent: Dec. 6, 2016

(54) DEVICE FOR MEASURING THE FREE CHLORIDE CONTENT OF WATER

(75) Inventors: Carine Beriet, Peseux (CH); Yves De Coulon, Wavre (CH); Cyrille Lemoine, Sartrouville (FR)

(73) Assignee: Veolia Water Solutions & Technologies Support, Saint-Maurice (FR)

( * ) Notice: Subject to any disclaimer, the term of this patent is extended or adjusted under 35 U.S.C. 154(b) by 427 days.

(21) Appl. No.: 14/234,921

(22) PCT Filed: Jul. 25, 2012

(86) PCT No.: PCT/EP2012/064601
§ 371 (c)(1),
(2), (4) Date: Sep. 19, 2014

(87) PCT Pub. No.: WO2013/014187
PCT Pub. Date: Jan. 31, 2013

(65) Prior Publication Data
US 2015/0068895 A1  Mar. 12, 2015

(30) Foreign Application Priority Data
Jul. 25, 2011 (FR) ..................... 11 56775

(51) Int. Cl.
*G01N 27/49* (2006.01)
*G01N 27/404* (2006.01)
*G01N 27/416* (2006.01)

(52) U.S. Cl.
CPC .......... *G01N 27/49* (2013.01); *G01N 27/4045* (2013.01); *G01N 27/4168* (2013.01)

(58) Field of Classification Search
CPC ................. G01N 27/27–27/32; G01N 27/333; G01N 27/40; G01N 27/49
USPC ............... 204/400, 415–420; 205/778.5–780
See application file for complete search history.

(56) References Cited

U.S. PATENT DOCUMENTS

| 5,393,399 A | * | 2/1995 | Van den Berg | .... G01N 27/4045 204/409 |
| 7,270,736 B2 | * | 9/2007 | Gobet | ................ G01N 27/4168 205/778.5 |
| 7,790,006 B2 | | 9/2010 | Feng et al. | |
| 2001/0042693 A1 | | 11/2001 | Onitskansky et al. | |
| 2012/0145561 A1 | | 6/2012 | Coulon et al. | |

* cited by examiner

*Primary Examiner* — Bach Dinh
(74) *Attorney, Agent, or Firm* — Coats and Bennett PLLC

(57) ABSTRACT

An amperometric sensor circuit for measuring chlorine concentration in water. The circuit includes first and second working electrodes coated with a hydrophilic membrane. A power supply and biasing circuit is configured to deliver a generally constant voltage between the first working electrode and a reference electrode and to generally deliver a constant current between the second working electrode and a counter electrode. A measurement circuit measures the current between the counter electrode and the first working electrode. A processing circuit is provided for determining the chlorine concentration based on the current measured by the measurement circuit.

14 Claims, 3 Drawing Sheets

DEVICE FOR MEASURING THE FREE CHLORIDE CONTENT OF WATER

This application is a U.S. National Stage Application of PCT Application No. PCT/EP2012/064601, with an international filing date of 25 Jul. 2012. Applicant claims priority based on French Patent Application No. 1156775 filed 25 Jul. 2011. The subject matter of these applications is incorporated herein.

1. FIELD OF THE INVENTION

The field of the invention is that of techniques for measuring physical/chemical properties of fluids, especially water such as for example potable water flowing in distribution networks.

More specifically, the invention pertains to the design and manufacture of probes and to methods for the in-line measurement of parameters representing the quality of water, especially its chlorine concentration.

2. THE PRIOR ART AND ITS DRAWBACKS

Chlorine is usually present in potable water in two forms:
the hypochlorous acid (HOCl) form also known as active chlorine;
the hypochlorite ions form (OCl—).

These two forms of chlorine coexist in water in proportions that depend on its pH according to the following dissociation equilibrium formula:

$$HOCl \leftrightarrows OCl^- + H^+$$

The sum of the concentrations in water of active chlorine on the one hand and in hypochlorite ions on the other hand constitute the concentration of free chlorine in this water:

$$[\text{Free chlorine}] = [HOCl] + [OCl^-]$$

The chlorine is injected into the potable water so as to obtain disinfection. The residual concentration of free chlorine in potable water at the distribution points at the consumer's premises must therefore be great enough to ensure that no bacterial growth is observed therein. It must however be weak enough so as not to affect its gustatory qualities.

The concentration of free chlorine in water is therefore a vital parameter in the assessment of its quality.

In water treatment, the quality of treated water is constantly controlled in order to verify the efficacy of its treatment and/or to optimize it according to the conditions of operation. Probes are generally implemented for this purpose.

There are known amperometric probes that are used to measure the chlorine concentration in the form of a hypochlorous acid of a water. These probes include for example a reference electrode, a working electrode and a counter electrode. The application of a difference in electric potential to the terminals of the reference and working electrodes reduces the hypochlorous acid and produces an electric current which can be measured at the terminals of the working electrode and the counter electrode. This current is proportional to the concentration of hypochlorous acid in water.

As explained here above, the concentration of chlorine in the form of hypochlorous acid and in the form of hypochlorite ions are related by the following reaction:

$$HOCl \leftrightarrows OCl^- + H^+$$

In addition, the pH value of water is related to its $H^+$ ion concentration by the formula:

$$pH = -\log([H^+]).$$

The coupling of a amperometric sensor of chlorine in the form of hypochlorous acid with a pH sensor leads therefore to obtaining a measurement device which can be used to know the concentration of hypochlorite ions in water and, from this, to deduce its free chlorine concentration. For memory, this is equal to the sum of its HOCl concentration and its OCl concentration.

A measuring device of this kind is advantageous in as much as it can be used to efficiently determine the free chlorine concentration of water which is a parameter subject to regulations on the quality of distributed potable water.

However, it has the drawback of requiring the implementation of a pH probe. This type of probe calls for frequent maintenance operations at a rate of less than a month per operation in order to benefit from the precision needed to compute free chlorine (0.01 pH units in the 6.5-9 pH units range), and this tends to increase the cost of this technique. The use of a pH probe also tends to reduce the compactness of such a measuring device.

The document US2005/0029103 describes another technique for measuring the free chlorine concentration of water by means of a probe comprising a cavity housing a working electrode and a reference electrode that bathe in an electrolyte containing a pH stabilizer. The cavity is closed off by a hydrophilic membrane that is permeable to both forms of chlorine constituting free chlorine. The hypochlorite ions that penetrate the cavity of the probe react therein to form hypochlorous acid. The application of a difference in electric potential at the terminals of the working electrode and the reference electrode reduces the hypochlorous acid and generates an electric current which is proportional to the hypochlorous acid concentration. By knowing the hypochlorous acid concentration and the pH in the cavity, it is possible to know the concentration of free chlorine in water.

This technique has the advantage of not requiring the implementing of a pH probe.

It nevertheless has the drawback of implementing an electrolyte.

The properties of such an electrolyte tend to get modified over time. It is therefore necessary to carry out regular maintenance campaigns to maintain such a measurement device in working condition. The service life of such a device, which is the time that elapses between its first implementation and the first maintenance operation is thus much shorter than one year.

Furthermore, the electrolyte should not be mixed with the treated water on which the measurements are made. However, a part of the electrolyte of this type of device can nevertheless leak into the water to be analyzed, with which it is put in contact. A bypass circuit should therefore be planned to enable a part of the treated water flowing in the distribution network to be diverted towards the measurement device, the diverted treated water being not reintroduced into the distribution network after the measurement has been made.

This technique therefore gives rise to additional costs related firstly to the implementing of such bypass means and secondly to the losses of treated water that are caused.

There is therefore no technique for measuring the concentration of free chlorine in a water, i.e. for measuring it directly in the distribution network and doing so in a simple and efficient way.

However, it can happen that the quality of the potable water deteriorates between its point of production and its point of distribution to the user. This can be caused for example by a break in a piping system, backflows or even deliberate intrusion of contaminants into the distribution network carried out by third parties.

Certain users therefore express the need to be able to directly verify the quality of the water distributed to them at the potable water distribution point in their homes or premises.

The prior art techniques do not enable such a need to be met.

3. GOALS OF THE INVENTION

The invention is aimed especially at overcoming these drawbacks of the prior art.

More specifically, it is a goal of the invention, in at least one embodiment, to provide a technique for carrying out the inline measurement of the free chlorine concentration of a water, i.e. directly in the water distribution network, for example with a measuring device in contact with this water.

It is another goal of the invention, in at least one embodiment, to propose such a technique which can be implemented during in a relatively lengthy period without any need to carry out maintenance campaigns.

In particular, it is a goal of the invention, in at least one embodiment, to implement a technique of this kind for which the frequency of the maintenance campaigns is greater than one year.

It is another goal of the invention, in at least one embodiment, to procure a technique of this kind that can be implemented with a reduced space requirement.

The invention also aims, in at least one embodiment, to provide a technique of this kind that can be implemented in pressurized conditions.

It is another goal of the invention in at least one embodiment to propose a technique of this kind that is reliable, simple and relatively economical to implement.

4. SUMMARY OF THE INVENTION

These goals as well as others that shall be achieved here below are achieved by means of a device for measuring the free chlorine content of a water, said device comprising at least one amperometric sensor of active chlorine comprising a reference electrode, a counter electrode, a first working electrode and a second working electrode, said reference electrode and said first working electrode being connected to means for generating a difference in electric potential, said counter electrode and said first working electrode being connected to means for measuring electric current, said counter electrode and second working electrode being capable of being linked to means for generating electric current, said device comprising a membrane coating said first and second working electrodes, said membrane being in contact with said working electrodes and comprising a gel capable of letting through hypochlorous acid (HOCl) and hypochlorite ions (OCl$^-$).

Thus, the invention relies on a wholly innovative approach which provides an amperometric sensor of active chlorine comprising two working electrodes coated with a membrane made of gel permeable to hypochlorous acid (HOCl) and hypochlorite ions (OCl). The hypochlorous acid and the hypochlorite ions can therefore diffuse through the membrane in order to achieve a concentration equilibrium between the exterior of the membrane and the interior. In other words, the concentration of hypochlorous acid and hypochlorite ions in the membrane is identical to that of the water in contact with the membrane.

The putting of the sensor into contact with the water whose free chlorine concentration is to be measured is accompanied by a diffusion of water and therefore of the hypochlorous acid and hypochlorite ions that it contains in the membrane. The composition of the water within the membrane is not disturbed by the flow of water circulating in the piping system on the surface of the membrane. The membrane therefore constitutes a stable diffusion layer for HOCl and the hypochlorite ions.

Since the working electrodes are in direct contact with the membrane, the application of an electric current to the terminals of a working electrode and of the counter electrode of the sensor generates the production of H$^+$ protons in the membrane by oxidation of water according to the formula $H_2O \rightarrow 2O_2 + 4H^+ + 4e^-$, and the reduction of the pH thereof.

By keeping the intensity of the generated current at a constant level, the production of protons produced will be constant whatever the quality of the water. To this end, the voltage at the terminals of this working electrode and the reference electrode could for example be modified in such a way that the intensity of the current at the terminals of this working electrode and the counter electrode will be constant whatever the conductivity of the water.

Under the effect of the production of protons, the hypochlorite ions present in the membrane get converted into hypochlorous acid according to the following reaction: HOCl$\leftrightarrows$OCl$^-$+H$^+$. The fact of reducing the pH in the membrane therefore moves the HOCl/OCl$^-$ equilibrium into a zone in which the active chlorine is predominant and its concentration is essentially identical to the free chlorine concentration as illustrated in FIG. 1.

The generation of a difference in electric potential, i.e. a voltage, at the terminals of the other working electrode and of the reference electrode reduces the active chlorine present in the membrane and generates an electric current proportional to its concentration in water according to the equation: HOCl+H$^+$+2e$^- \rightarrow$ Cl$^-$+H$_2$O. The electric current generated can be measured at the terminals of this other working electrode and the counter electrode.

Given the stable diffusion layer created by the membrane, the measured electric current is stationary and proportional to the HOCl concentration of water present in the membrane.

Whatever the shape of the electrodes, a linear regression can be determined during a step of calibration that can be carried out in the factory during the manufacture of the sensor. This calibration step consists in plunging the sensor into two or more solutions having known and different values of pH and free chlorine or active chlorine concentration. The chlorine measured by the sensor is proportional to the active chlorine concentration of the solutions in which the sensor is plunged. Should the active chlorine concentrations of the solutions be known, it is possible, for each solution, to associate an active chlorine concentration with an intensity of current generated. Should the free chlorine concentration be known, it is possible, for each solution, to determine the active chlorine concentration, for example according to the following formula:

$$[\text{Free chlorine}] = [\text{Active chlorine}](1 + 10^{\wedge}(-\log([H^+] + C.i) - pKa))$$

where:

i is the intensity of the generated current measured;

C is a constant related to the shape of the electrodes.

This step of calibration can be used to obtain a linear regression line relating the active chlorine concentration to the intensity of the current generated. The active chlorine corresponding to a given current can then be computed from this line.

In the context of circular electrodes, the theory enables the direct computation of the constant C according to the formula: $C=1/(4nFDr)$ where:
- n: Number of electrons from the oxidation-reduction reaction (n will be preferably equal to 2);
- F: Faraday constant;
- D: coefficient of diffusion determined in the laboratory for the type of membrane chosen (generally ranging from $10^{-5}$ to $10^{-6}$ cm$^2$/s);
- R: radius of the electrode.

In general, the value of the constant C can be determined during a calibration step. This step consists in plunging the sensor into a solution whose pH ($pH=-\log([H+])$), free chlorine concentration and current i generated are known. In these specific cases, the free chlorine concentration is computed or can be measured by means of a reference sensor (using the DPD method and a pH electrode). The value of the currents measured by the sensor as well as the formula here below can be used to compute the constant C which is the only unknown:

$$[\text{Free chlorine}]=[\text{Active chlorine}](1+10^{\wedge}(-\log([H^+]+C.i)-pKa))$$

The active chlorine concentration measured according to the invention corresponds appreciably to the free chlorine concentration of the water to be analyzed.

The implementing of the technique according to the invention thus makes it possible to know the free chlorine concentration of a water to be analyzed by approximation without using either an electrolyte or a pH sensor.

The implementing of the membrane efficiently protects the working electrodes against fouling. In addition, a device according to the invention does not require the implementing of a consumable electrolyte. A device according to the invention benefits therefore from a service life of over one year, i.e. it can enable the measurement the free chlorine concentration of water for more than one year without any need to carry out maintenance operations.

Since it does not use means for measuring pH, a device according to the invention is furthermore highly compact. The implementing of the membrane additionally makes it possible to measure the free chlorine concentration in pressurized conditions. A device according to the invention can thus be installed in a network for distributing potable water, for example directly in a user's premises. The quality of the potable water can therefore be verified up to its point of distribution.

The technique according to the invention does not require the construction of a network for re-routing a part of the water to be analyzed since it does not use any electrolyte, i.e. the sensor does not contain any reagent. Thus, losses of potable water are prevented. This reduces the cost of implementing the measurement of the free chlorine in water.

Said membrane is preferably made of a polymer such as for example Poly(2-hydroxyethylmethacrylate), agarose, polyvinyl alcohol (PVA) . . . .

A gel of such a polymer has the advantage of enabling efficient diffusion of active chlorine, hypochlorite ions and Cl$^-$ ions. It is in other words permeable to active chlorine, hypochlorite ions and Cl$^-$ ions.

In one preferred embodiment of the invention, a device according to the invention comprises means for driving in order to implement or not implement said means for generating an electric current for a certain duration.

It is thus possible to measure the active chlorine concentration of water without implementing the means for generating electric current, i.e. without modifying the pH in the membrane and then measuring its free chlorine concentration by approximation in implementing said means for generating an electric current. It is then possible to compute the concentration of hypochlorite ions in the water and the value of its pH.

The value of the pH can be determined by applying the following:

$$pH=pKa+\log\{([\text{Free chlorine}]-[\text{Active chlorine}])/[\text{Active chlorine}]\}$$

where pKa is the dissociation equilibrium constant of the pair HOCl/OCl— which is known and is equal to 7.55 to 25° C.

In another advantageous embodiment, a device according to the invention comprises a second amperometric sensor of active chlorine.

According to a first variant of such an embodiment, said first and second amperometric sensors of active chlorine are identical. They are then two four-electrode amperometric chlorine sensors.

In this case, when the means for generating an electric current connected each sensor are implemented, they deliver currents of different intensities $i_1$ and $i_2$. It will then be possible to determine the free chlorine concentration of the water and the value of its pH.

The free chlorine concentration can be computed by applying for example the following formula:

$$[\text{Free chlorine}]=[\text{Active chlorine}]_{1 \text{ or } 2}(1+10^{\wedge}(-\log([H^+]+C.i_{1 \text{ or } 2})-pKa))$$

Active chlorine]$_1$[ and [Active chlorine]$_2$ are determined by the measurement of the current generated during the reduction of the HOCl species and the application of a current with an intensity respectively of $i_1$ or $i_2$ between the counter electrode and one of the working electrodes of an amperometric sensor.

[H$^+$] is the concentration of protons present in water.

The pH of the water can be computed by applying for example the following equations where the single unknown quantity is the concentration in protons [H$^+$]:

$$[\text{Active chlorine}]_2/[\text{Active chlorine}]_1=(1+10^{\wedge}(-\log([H^+]+C.i_1)-pKa))/(1+10^{\wedge}(-\log([H^+]+C.i_2)-pKa))$$

and $$pH=-\log([H^+])$$

where:
- the pKa is the dissociation equilibrium constant of the HOCl/OCl$^-$ pair which is known and is equal to 7.55 to 25° C.;
- [H$^+$] is the concentration of proton present in water;
- C is a known constant which depends on the geometry of the electrodes;
- [Active chlorine]$_2$ and [Active chlorine]$_1$ are two values of concentration in hypochlorous acid measured in the membrane by both sensors.

According to a second variant of such an embodiment, the second amperometric sensor of active chlorine comprises a reference electrode, a counter electrode and a single working electrode, said reference electrode and working electrode being capable of being connected to second means for generating a difference in electric potential, said working electrode and counter electrode being connected to second means of measurement of the current.

Free chlorine concentration of water can then be determined by means of the four-electrode amperometric sensor and the active chlorine concentration of the water can simultaneously be determined by means of the three-electrode amperometric sensor. From this, it is possible to deduce the concentration of the water in hypochlorite ions and the value of its pH.

A device according to the invention could comprise means for controlling the value of the intensity of the electric current delivered by said means for generating an electric current.

The properties of resistivity and conductivity of a water can vary. These properties have an influence on the difference in potential that has to be applied between the second working electrode and the reference electrode so that the intensity of the current flowing between the second working electrode and the counter electrode are constant and so that the production of protons in the second working electrode is constant. Indeed, the greater the resistivity of the water, i.e. the lower its conductivity, the greater is the difference in potential to be applied between the second working electrode and the reference electrode. The implementing of such controlling means therefore makes it possible to ensure that the quantity of data delivered to the second working electrode is constant and that the same is true for the variation in pH.

Said working electrodes could advantageously take the shape of disks.

Such electrodes have the advantage of being less costly to manufacture. Their implementation therefore enables the production of a device for measuring at a more competitive price.

They could also advantageously take the form of combs. This geometry permits a greater production of protons and is particularly suited to water whose pH is higher (>8 units pH) and where it is necessary to apply a relatively greater reduction of pH.

5. LIST OF FIGURES

Other features and advantages of the invention shall appear more clearly from the following description of preferred embodiments, given by way of simple illustratory and non-exhaustive examples and from the appended drawings, of which:

6. DESCRIPTION OF ONE EMBODIMENT OF THE INVENTION

6.1. Reminder of the Principle of the Invention

The general principle of the invention relies on the implementing of an amperometric sensor of active chlorine comprising two working electrodes coated with a membrane capable of letting HOCl and OCl⁻ pass through, in order to determine the free chlorine concentration of water in modifying the pH within the membrane by generating protons.

6.2. Example of a Device for Measuring According to the Invention

6.2.1. Architecture

Figure 1:
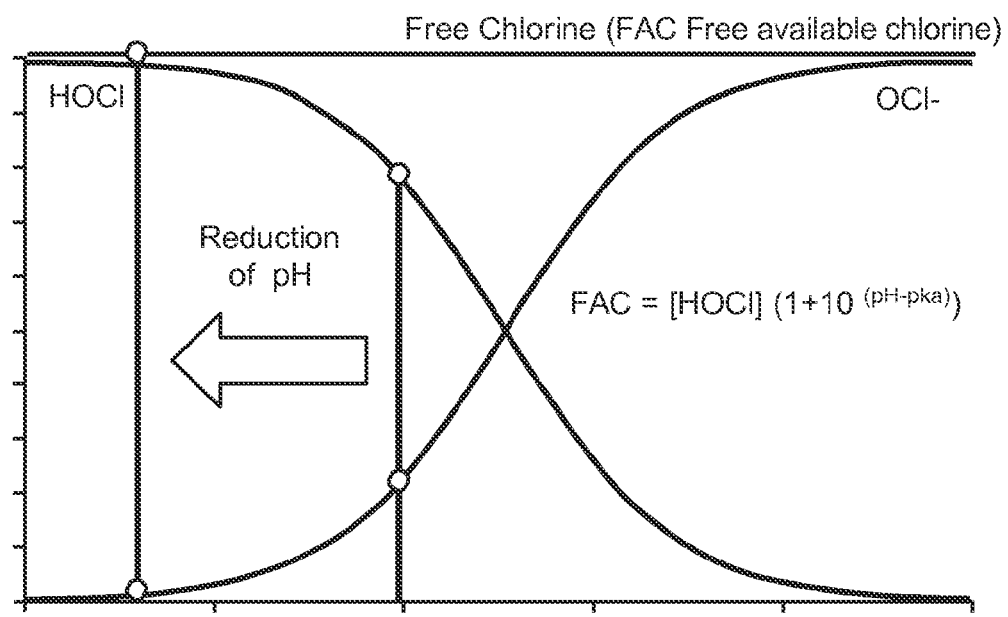
FIG. 1 illustrates the equilibrium curves for chlorine in the form of hypochlorous acid and hypochlorite ions as a function of the pH.
Figure 2:
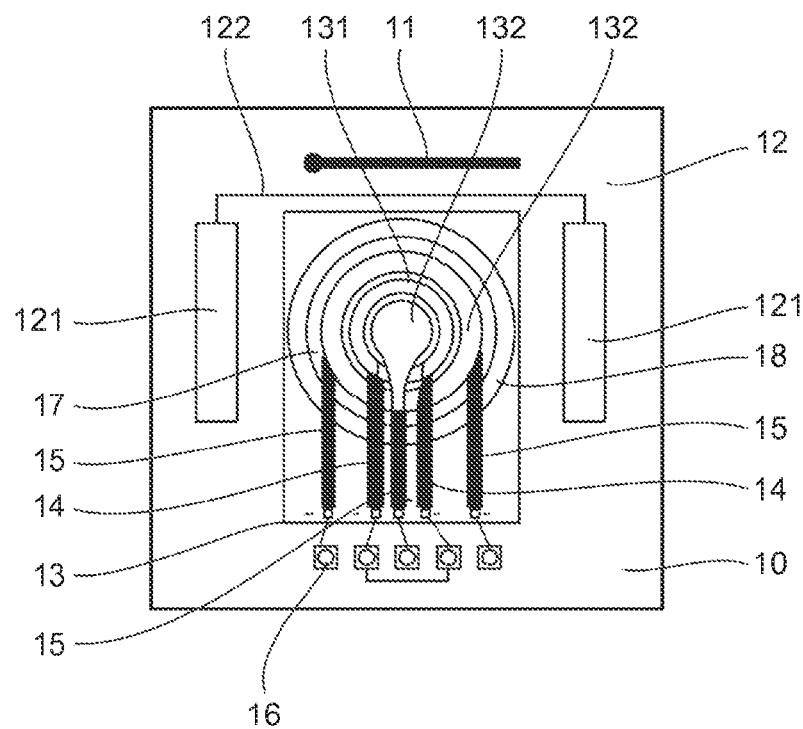
FIG. 2 illustrates a chip of a device according to the invention mounted on a printed circuit.

Referring to FIG. 2, we present an embodiment of a device for measuring the free chlorine concentration of a water.

As shown in this FIG. 2, such a device comprises a printed circuit 10.

A reference electrode 11 is mounted on the printed circuit 10. In this embodiment, this reference electrode 11 is an Ag/AgCl reference pseudo-electrode.

A counter electrode 12 is mounted on the printed circuit 10. In this embodiment, this counter electrode 12 comprises two semi-electrodes 121 connected to one another by means of a conductive track 122 made on the printed circuit 10. The counter electrode 22 is made out of a stainless steel plate.

The measuring device comprises an essentially quadrangular chip 13. This chip 13 is made of silicon. It has a first working electrode 131 and a second working electrode 132.

The first working electrode 131 comprises two connection pads 14. It has the shape of a ring.

The second working electrode 132 has three connection pads 15. It takes the form of a disk crossed by a recess. The dimensions of this recess are such that it can house the ring of the first working electrode 131 without the first working electrode 131 and second working electrode 132 being in contact with each other. The first and second working electrodes 131, 132 are made out of platinum. They are not microelectrodes.

The chip 13 has a polymer ring 18 designed to facilitate its encapsulation on the printed circuit 10. This ring is made out of polysiloxane (PX).

The first and second working electrodes 131, 132 are coated with a membrane 17. The membrane 17 is made out of gel. It is a polyHEMA membrane. It is made out of a Poly(2-hydroxyethylmethacrylate) polymer. This membrane is hydrophilic, i.e. it can get impregnated with water. It can let through the hypochlorite ions and the hypochlorous acid. In other words, the hypochlorite ions and the hypochlorous acid can get diffused within the membrane and achieve equilibrium concentration with the medium in which the measurement is being made. This is therefore a partially selective membrane. In this embodiment, this membrane is also permeable to Cl⁻ ions.

The membrane 17 is connected to the working electrodes 131, 132 by covalent bonds. It has a thickness preferably ranging from 40 to 150 micrometers.

The rest of the chip 13 is coated with an insulator which, in this embodiment, is constituted by silicon nitride.

The printed circuit 10 comprises connection pads 16 which are connected by wires to the connection pads 14, 15 of the chip 13.

The greater the number of pads, the greater is the reliability of the connection between the chip and the printed circuit.

The measuring device comprises means for generating a difference in electric potential (not shown). These means for generating a different in electric potential comprise a voltage generator to apply a constant voltage between the terminals of the reference electrode 11 and the first working electrode 131 via the connection pads. In this embodiment, the voltage generator is connected to the reference electrode 11 and to the first working electrode 131.

The measuring device comprises means for generating an electric current (not shown). These means for generating an electric current comprise a current generator and enable the application of an electric current between the terminals of the counter electrode 12 and the second working electrode 132 via the connection pads. In this embodiment, the application of a current of constant intensity between the counter electrode 12 and the second working electrode 132 is obtained by the implementing of a variable voltage generator at the terminals of the reference electrode 11 and the second working electrode 132.

The measuring device furthermore comprises means for controlling the value of the intensity of the electric current delivered by the means for generating an electric current. In this embodiment, these control means automatically modify the value of the voltage applied by the current generation means according to the resistivity or conductivity of water, the free chlorine concentration of which is measured in such a way that the intensity of the electric current delivered by the means for generating current are constant and the generation of protons at the second working electrode is constant.

In this embodiment, the means for generating a difference in electric potential and the means for generating electric current constitute a common power supply and biasing circuit, also called a bipotentiostat. Such a bipotentiostat enables the delivery of constant voltage between the first working electrode and the reference electrode and a constant current between the second working electrode and the counter electrode. Its implementing makes it possible to use only one counter electrode and only one reference electrode. In one variant, the means for generating a difference in potential and the means for generating an electric current could be independent of each other. They could for example be each constituted by a potentiostat.

A potentiostat can be implemented in different operational modes. The selection of an amperometric mode induces the application of a difference in fixed potential (between the working electrode and the reference electrode) and the measurement of current (between the working electrode and the counter electrode). The selection of a potentiostat mode induces the application of a fixed current (between the working electrode and the counter electrode) and the measurement of the difference in potential (between the working electrode and the reference electrode). In this embodiment, the bipotentiostat used is from Palm Instruments BV (reference: Palmsens with bipotentiostat). Other types of potentiostat can be used in variants.

The measuring device comprises means (not shown) for measuring current between the terminals of the counter electrode 12 and the terminals of the first working electrode 131 via the connection pads. These means for measuring can for example include a voltmeter or an ammeter. They are connected to means for analyzing which make it possible to determine the active chlorine concentration from the value of the current measured via the measuring means. These means for analyzing can for example comprise one or more computers, for example processors.

The means for generating a difference in potential, the means for generating an electric current, the means for measuring current, the means for analysis and the chip 13 which comprise the first working electrode 131 and second working electrode 132, the counter electrode 12 and the membrane 17 constitute a first four-electrode amperometric sensor of active chlorine that can be implemented to measure the free chlorine concentration of a water by equivalence.

In this embodiment, the diameter on the chip of the first working electrode preferably ranges from 1900 to 2600 micrometers, the diameter on the chip of the second working electrode is preferably equal to 4200 micrometers, the difference between the external diameter and the internal diameter of the polymer ring is preferably equal to 500 micrometers, the structure of the chip preferably has a length and a width respectively equal to 8 and 6 millimeters, the diameter of the insulation is preferably equal to 3100 micrometers.

6.2.2. Variants

Figure 3:
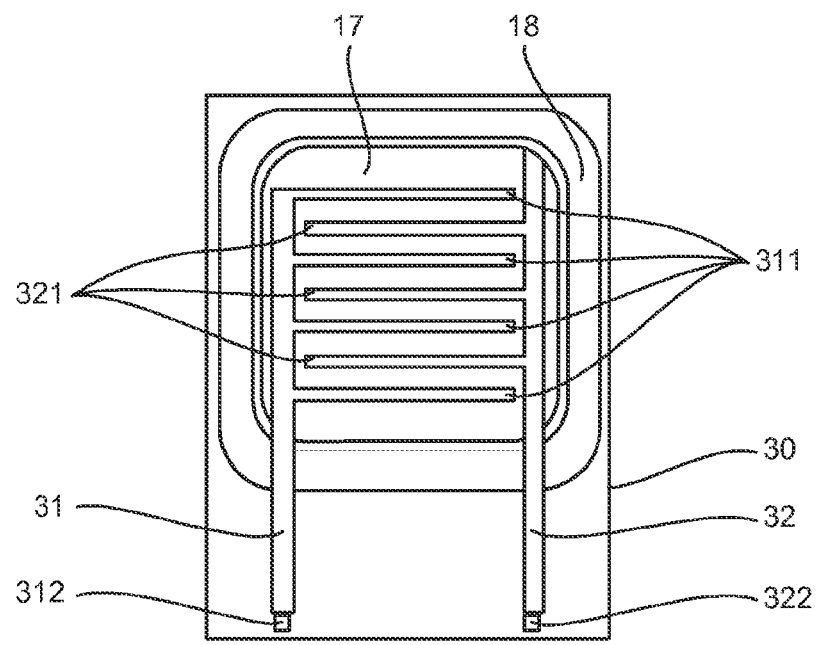
FIG. 3 illustrates a variant of the chip shown in FIG. 2.

FIG. 3 illustrates one variant of a chip 30 of a device for measuring according to the invention. As shown in this FIG. 3, such a chip 30 is essentially quadrangular. It comprises a first working electrode 31 and a second working electrode 32 which are each constituted by a plurality of wires or combs 311, 321 disposed in parallel to one another. These working electrodes 31, 32 comprise connection pads 312, 322 for connection to the printed circuit 10. The zones situated between the combs are constituted by platinum coated with silicon nitride. The electrodes in the form of combs could be microelectrodes having a size smaller than 100 micrometers. In this variant, the first working electrode preferably has dimensions of 100 micrometers by 3400 micrometers, the second working electrode preferably has dimensions of 160 micrometers by 3600 micrometers, the difference between the external diameter and the internal diameter of the polymer ring is preferably equal to 500 micrometers, the structure of the chip preferably has a length and a width respectively equal to 8 and 6 millimeters, the diameter of the insulation is preferably equal to 110 micrometers.

Figure 5:
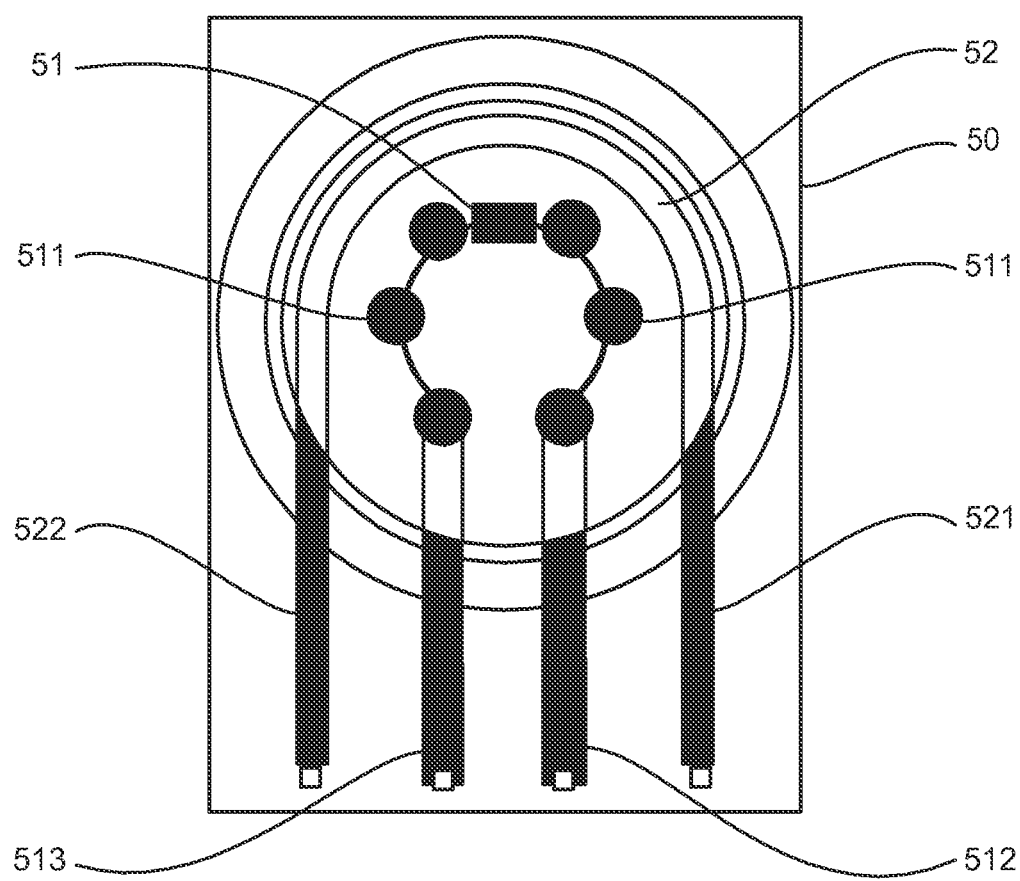
FIG. 5 illustrates a variant of the chip illustrated in FIG. 2.

FIG. 5 illustrates another variant of a chip 50 according to the invention. As shown in this FIG. 5, such a chip 50 is essentially quadrangular. It comprises a first working electrode 51 which comprises a plurality of electrode portions in the form of disks 511 laid out at the centre of the chip in a circular manner. It comprises a second working electrode 52 disposed semi-circularly around the first working electrode 51. These working electrodes 51, 52 comprise connection pads 521, 522, 512, 513 for connection to the printed circuit 10. In this variant, the first working electrode preferably has a diameter on the chip equal to 600 micrometers, the second working electrode preferably has a diameter on the chip equal to 4200 micrometers, the difference between the external diameter and the internal diameter of the polymer ring is preferably equal to 500 micrometers, the structure of the chip preferably has a length and a width respectively equal 8 and 6 millimeters, the insulation diameter is preferably equal to 900 micrometers.

In the variants, the reference electrode 11 and the counter electrode 12 could be directly integrated into the chip 13, 30.

The measuring device can furthermore comprise means for driving means for generating electric current. These means for driving enable the implementation or non-implementation of the means for generating current for a certain period of time. In one alternative, they can enable the means for generating current to generate a first current of constant intensity by application of a first difference in electric potential for a certain period of time and then a second current of a constant intensity by the application of a second difference in electric potential for another duration.

In another variant, the device of the invention could furthermore comprise a second sensor of active chlorine comprising a single working electrode, a reference electrode, a counter electrode, means for generating a difference in electric potential at the terminals of the working electrode and the reference electrode and means for measuring current at the terminals of the working electrode and the counter electrode. This is a three-electrode amperometric sensor of active chlorine.

In another variant, a device according to the invention could include two identical four-electrode amperometric sensors of active chlorine. The means for generating current connected to each of these sensors will enable the delivery of a different voltage between one of the working electrodes and the reference electrodes of each of these sensors.

In these last two variants, it will not be necessary to implement means for driving the means to generate electric current of each sensor so as to implement or not implement the second means for generating during a certain period of time.

6.3. Example of a Method for Measuring the Free Chlorine Concentration of Water 6.3.1. Measurement of the Free Chlorine Concentration of Water A method for measuring the free chlorine concentration of water according to the invention shall now be described.

A device for measuring according to the invention can be connected directly to a potable water distribution pipe in order to measure the free chlorine concentration of the water that flows therein.

The device for measuring is positioned in such a way that the membrane is housed in the pipe and comes into contact with the water that flows therein.

In contact with water, the membrane 17 of the chip 13 becomes saturated with water. The membrane 17 lets the hypochlorite ions and the active chlorine present in the water pas through.

The means for generating an electric current are implemented so as to generate a constant electric intensity between the second working electrode 132 and the counter electrode 12 by the application of a variable difference in potential to the terminals of the second working electrode 132 and the reference electrode 11. A generation of protons in the form of $H^+$ ions is then observed in the second working electrode 132 by oxidation of water according to the following equation: $H_2O \rightarrow 2O_2 + 4H^+ + 4e^-$. These protons get diffused inside the membrane 17. The pH of the water imbibed into the membrane is reduced so that the chlorine present in the membrane is essentially in the form of active chlorine therein. Indeed, the hypochlorite ions react with the $H^+$ ions to form hypochlorous acid.

There is a gradient of active chlorine concentration inside the membrane, the concentration being zero in contact with the working electrodes.

The means for generating a difference in electric potential are also implemented so as to apply a constant voltage to the terminals of the first working electrode 131 and the reference electrode 11. The active chlorine HOCl present in the membrane 17 is then reduced according to the equation: $HOCl + H^+ + 2e^- \rightarrow Cl^- + H_2O$. The reduction of the active chlorine is accompanied by the generation of an electric current whose value is proportional to the active chlorine concentration of the membrane 17 and therefore the water flowing in the potable water piping system.

The implementing of a means for measuring makes it possible to measure the current generated by the generation of active chlorine at the terminals of the first working electrode 131 and the counter electrode 12.

The means of analysis therefore make it possible, according to the current measured by the measuring means, to determine the active chlorine concentration within the membrane. This is done on the basis of the linear regression line relating the active chlorine concentration with the intensity of the generated current obtained during the calibration of the sensor.

Given the low value of the pH in the membrane, the free chlorine concentration is appreciably equal to the active chlorine concentration of water. The free chlorine concentration of water is therefore determined by approximation.

6.3.2. Measurement of the pH and Free Chlorine Concentration of Water

A method according to the invention can also be implemented to measure the free chlorine concentration of a water as well as the value of its pH.

In this case, the measuring device implements:
either a single four-electrode amperometric sensor of active chlorine and means for driving the means for generating an electric current;
or a four-electrode amperometric sensor of active chlorine and a three-electrode amperometric sensor of active chlorine;
or two identical four-electrode amperometric sensors of active chlorine.

A. Single Four-Electrode Amperometric Sensor of Active Chlorine and Means for Driving Means for Generating an Electric Current A first step consists in measuring the active chlorine concentration in the membrane without modifying the pH thereof.

To this end, the means for driving are implemented in such a way that no electric current is generated by the means for generating current at the terminals of the second working electrode 132 and the counter electrode 12.

The means for generating a difference in electric potential are implemented so as to generate a difference in electric potential at the terminals of the first working electrode 131 and the reference electrode 11. The active chlorine present in the membrane is then reduced, thus generating an electric current whose value is measured by the means for measuring at the terminals of the first working electrode 131 and the counter electrode 12.

The means for analyzing then determine the active chlorine concentration of the water present in the membrane as described here above from the current measured at the terminals of the first working electrode 131 and the counter electrode 12.

A second step consists in measuring the free chlorine concentration of the water present in the membrane by approximation in modifying its pH as described here above. The driving means are then implemented so that the means for generating an electric current apply a voltage to the terminals of the second working electrode 132 and the reference electrode 11 so as to generate a constant current between the second working electrode 132 and the counter electrode 12.

The means for analyzing determine the free chlorine concentration of the water by approximation from the current measured at the terminals of the first working electrode 131 and the counter electrode 12 as explained here above.

The means for analyzing then determine the pH of the water circulating in the piping system from its active chlorine concentration and its free chlorine concentration according to the formula:

$$pH = pKa + \log\{([\text{Free chlorine}] - [\text{Active chlorine}])/[\text{Active chlorine}]\}$$

where the pKa is the dissociation equilibrium constant of the $HOCl/OCl^-$ pair which is known and is equal to 7.55 to 25° C.

The means for analyzing can also determine the hypochlorite ion concentration of the water from its free chlorine concentration and its active chlorine concentration.

B. Four-Electrode Amperometric Sensor of Active Chlorine and Three-Electrode Amperometric Sensor of Active Chlorine The free chlorine concentration of the water is determined by approximation by means of the four-electrode sensor as explained here above.

At the same time, the active chlorine concentration of the water is determined by the use of the three-electrode amperometric sensor of active chlorine. To this end, a voltage is applied by means for generating a difference in electric potential at the terminals of the working electrode and the reference electrode of the three-electrode sensor. This is accompanied by a reduction of the active chlorine and the generation of an electrical current proportional to the active chlorine concentration of the water. This current is measured at the terminals of the working electrode and the counter electrode of the three-electrode sensor. The means of analysis then determine the active chlorine concentration of water from the measurement of current generated at the terminals of the working electrode and the counter electrode of the three-electrode sensor. To this end, the three-electrode active chlorine sensor is calibrated relative to a reference as explained previously for a four-electrode sensor so as to obtain a linear regression line that relates the active chlorine concentration to the intensity of generated current measured.

From the free chlorine concentration and the active chlorine concentration of the water the means for analyzing determine the pH of the water as indicated here above.

From the free chlorine concentration and the active chlorine concentration of the water, the means for analyzing can also determine the hypochlorite ion concentration of the water.

C. Two Identical Four-Electrode Amperometric Sensors of Chlorine

A first step consists in measuring the active chlorine concentration of the water present in the membranes by modifying the pH therein as described here above to reach a first value of pH. The driving means are then implemented so that the means for generating electrical current apply a first voltage to the terminals of the second working electrode 132 and the reference electrode 11 of a first amperometric sensor so that the intensity of the current generated between the second working electrode and the counter electrode of the first sensor is constant.

The means for analysis determine a first active chlorine concentration of the water from the first general current measured at the terminals of the first working electrode 131 and the counter electrode 12 of the first amperometric sensor as explained here above.

A second step consists in measuring the active chlorine concentration of the water present in the membrane in modifying the pH therein as described here above, to reach a second value of pH. The driving means are then implemented so that the means for generating electrical current apply a second voltage to the terminals of the second working electrode 132 and the reference electrode 11 of the second amperometric sensor so that the intensity of the current generated between the second working electrode and the counter electrode of the second sensor is constant.

The means for analyzing determine a second active chlorine concentration of water from the second current measured at the terminals of the first working electrode 131 and the counter electrode 12 of the second amperometric sensor as explained here above.

The first and second steps are preferably implemented concomitantly.

The means for analyzing then determine the pH of the water circulating in the piping system by applying the following formula where the single unknown is the proton concentration [$H^+$]:

$$[\text{Active Chlorine}]_2/[\text{Active Chlorine}]_1 = (1+10^{\wedge}(-\log([H^+]+C.i_1)-pKa))/(1+10^{\wedge}(-\log([H^+]+C.i_2)-pKa))$$

then the following formula:

$$pH = -\log([H^+])$$

[Active Chlorine]$_2$ and [Active Chlorine]$_1$ are the two values of hypochlorous acid concentration measured in the membrane by the two sensors.

The means for analyzing can also determine the free chlorine concentration of water according to either of the following formulae:

$$[\text{Free chlorine}] = [\text{Active chlorine}]_2(1+10^{\wedge}(-\log([H^+]+C.i_2)-pKa))$$

Or:

$$[\text{Free chlorine}] = [\text{Active chlorine}]_1(1+10^{\wedge}(-\log([H^+]+C.i_1)-pKa))$$

The means of analysis can also determine the active chlorine concentration of water according to the following formula:

$$[\text{Active chlorine}] = [\text{Free chlorine}]/(1+10^{\wedge}(pH-pKa))$$

the pH being determined by the previous formula.

In one variant, the free chlorine concentration and the pH of the water could be determined by following the same principle and implementing only one four-electrode amperometric sensor connected to means for controlling second means for generating acting on these means in such a way that they deliver a first voltage for a certain time and then another voltage.

6.4. Trials

Trials were conducted to verify the efficacy of a technique for measuring the free chlorine concentration chlorine of water according to the invention.

In a first step, a device according to the invention was put into contact with water containing no chlorine and with a pH ranging from 8.2 to 8.4. An emission of protons was maintained at the second working electrode. The intensity of the current at the terminals of the first working electrode and the reference electrode were then zero.

Figure 4:
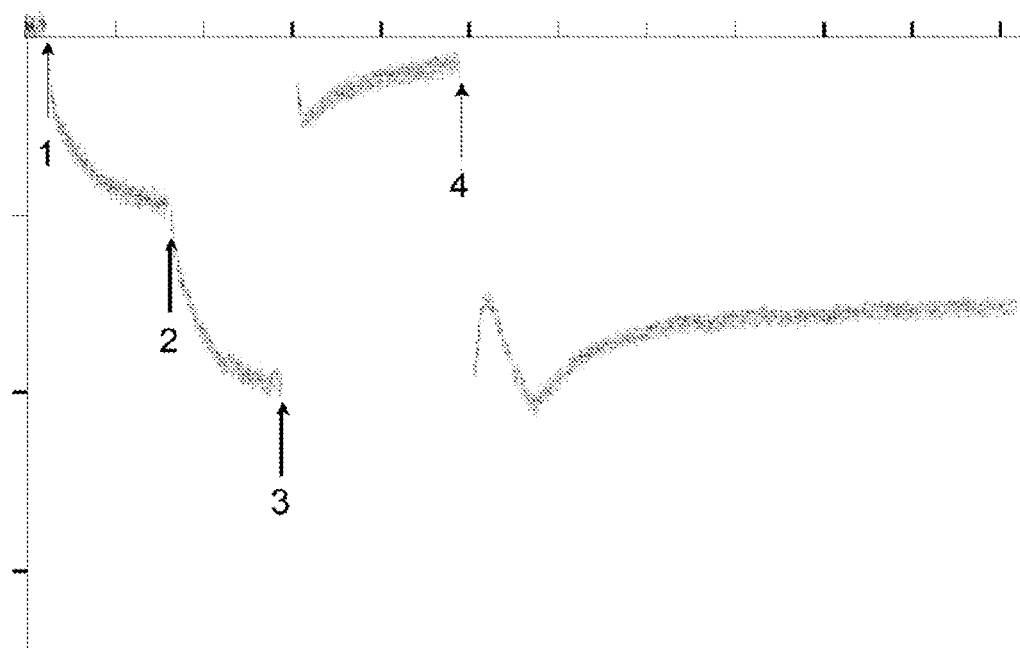
FIG. 4 illustrates the variation, as a function of time, of the intensity of the current measured by means of a device according to the invention.

An identical number of drops of a hypochlorite solution was introduced twice into the water (arrows 1 and 2 in FIG. 4). It is seen then that the intensity of the current at the terminals of the first working electrode and the counter electrode is proportional to the quantity of hypochlorite solution injected into water.

The production of protons at the second working electrode was then stopped (see arrow 3 in FIG. 4). This was accompanied by a drop in the intensity of the current at the terminals of the first working electrode and the counter electrode to a value close to zero. This expresses the fact that the stoppage of the generation of protons in the membrane was accompanied by a stoppage of the conversion of hypochlorite ions into hypochlorous acid.

The resumption of the generation of protons (see arrow 4 in FIG. 4) was again accompanied by the generation of a current, of which the intensity measured at the terminals of the first working electrode and the counter electrode was proportional to the quantity of hypochlorite ions present in the water.

This trial clearly showed that the generation of protons in the membrane made it possible to convert the hypochlorite ions into hypochlorous acid and thus to shift the hypochlorous acid/hypochlorite ions equilibrium into a zone in which the hypochlorous acid concentration is appreciably equal to the free chlorine concentration.

The height of the stages obtained in response to the injections of a same quantity of hypochlorite solution is identical. The measurement of the current generated in response to these injections is therefore linear.

6.5. Other Advantages

The technique of the invention makes it possible to measure the free chlorine concentration of a water by approximation in lowering its pH in such a way that the active chlorine form of chlorine is preponderant and that its concentration is appreciably equal to that of the free chlorine.

The technique can especially be efficiently implemented by lowering the pH of the water to a value ranging from 5.5 to 6.5.

The invention claimed is:

1. Device for measuring the chlorine content of a water, said device comprising at least one amperometric sensor of chlorine comprising a reference electrode, a counter electrode, a first working electrode and a second working electrode, said reference electrode and said first working electrode being connected to a voltage generator for generating a difference in electric potential, said counter electrode and said first working electrode being connected to a current measuring device for measuring electric current, said counter electrode and said second working electrode being linked to a current generator for generating electric current, said device further comprising a membrane coating said first and second working electrodes, said membrane being in contact with said working electrodes and comprising a gel permeable to hypochlorous acid (HOCl) and to hypochlorite ions (OCl$^-$).

2. The device of claim 1 characterized in that said membrane is made of a polymer.

3. The device according to claim 2 characterized in that said polymer is Poly(2-hydroxyethyl methacrylate).

4. The device according to claim 1 characterized in that the device comprises a variable voltage generator for driving in order to implement or not implement said current generator.

5. The device according to claim 1 characterized in that the device comprises a second amperometric sensor of chlorine.

6. The device according to claim 5 characterized in that said first and second amperometric sensors of chlorine are identical.

7. The device according to claim 5 characterized in that said second amperometric sensor of chlorine comprises a second reference electrode, a second counter electrode and a single working electrode, said second reference electrode and second working electrode being connected to a second voltage generator for generating a difference in electric potential, said second working electrode and second counter electrode being connected to a second current measuring device for measuring current.

8. The device of claim 1 characterized in that the device comprises a variable voltage regulator for controlling the value of the intensity of the electric current delivered by said current generator.

9. The device according to claim 1 characterized in that said working electrodes assume the shape of disks.

10. The device according to claim 1 characterized in that said working electrodes assume the form of combs.

11. The amperometric sensor circuit of claim 1, wherein the power supply and biasing circuit comprises a biopotentiostat.

12. The amperometric sensor circuit of claim 1, wherein the power supply and biasing circuit comprises:
a first potentiostat configured to deliver the constant voltage between the first working electrode and the reference electrode; and
a separate, second potentiostat configured to deliver the constant current between the second working electrode and the counter electrode.

13. The amperometric sensor circuit of claim 1, wherein the measurement circuit comprises a voltmeter or ammeter.

14. An amperometric sensor circuit operative to measure a chlorine concentration of water, comprising:
first and second working electrodes that are each coated with a respective hydrophilic membrane;
a power supply and biasing circuit configured to, based on a resistivity or conductivity of water in contact with the hydrophilic membranes, deliver a constant voltage between the first working electrode and a reference electrode, and to deliver a constant current between the second working electrode and a counter electrode;
a measurement circuit configured to measure a current between the counter electrode and the first working electrode; and
a processing circuit operatively connected to the measurement circuit, and configured to determine a chlorine concentration of the water based on the current measured by the measurement circuit.

* * * * *